Sept. 27, 1966 H. W. MOTZKAU Plant Pat. 2,672
AZALEA PLANT
Filed March 19, 1965
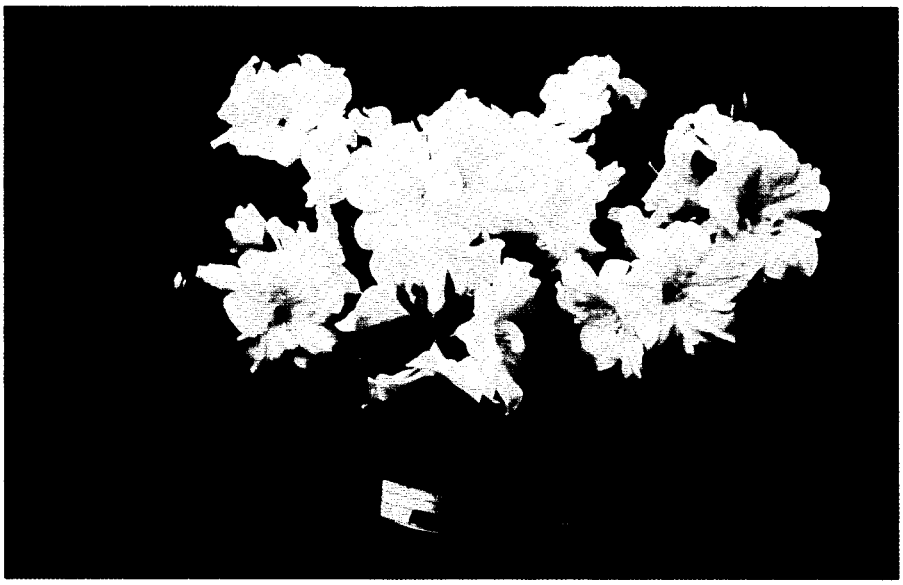
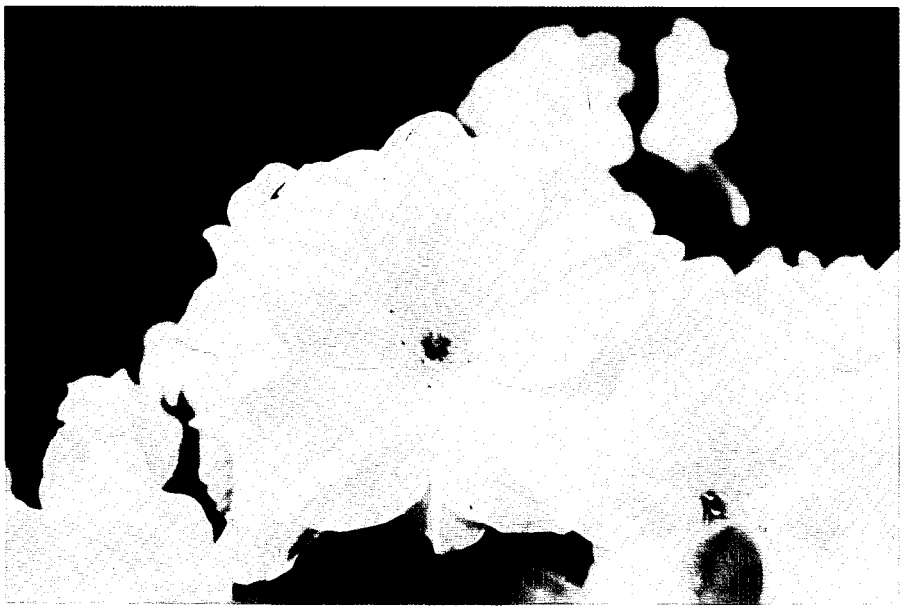
Inventor:
Henry W. Motzkau
by Robb & Robb
attorneys United States Patent Office Plant Pat. 2,672
Patented Sept. 27, 1966

2,672
AZALEA PLANT

Henry W. Motzkau, Whitewater, Wis., assignor to Yoder Brothers, Inc., Barberton, Ohio, a corporation of Ohio Filed Mar. 19, 1965, Ser. No. 441,387
1 Claim. (Cl. Plt.—57)

My present invention relates to a new and distinct variety of azalea plant which has been produced by crossing certain varieties which I have developed, in a program of hybridization, the parent varieties being designated as Nancy Kay, and Rosa, neither being a patented variety.

The object of the present invention has been to produce a new variety of azalea plant which will have a distinctive color and earliness of bloom with vigorous growth and large flowers.

I have endeavored to eliminate certain of the problems which have arisen in the production and growth of the seed parent Nancy Kay, which seed parent had very low tolerance to salt, the instant variety having substantially greater tolerance therefor and not being thus adversely influenced thereby.

In the extensive program of hybridization which has resulted in the instant variety along with others of comparable value, I have endeavored to select plants which set buds readily and can be brought to bloom early without artificially inducing dormancy.

In the particular program which I have generally discussed hereinbefore, the selection and crossing of nameless seedlings was undertaken and as a result of the crossings and inter-crossings the instant variety was ultimately selected because of its color and earliness of bloom as heretofore suggested.

Although the natural blooming period of the instant variety of azalea plant is from early mid-season, it can be flowered the year around by manipulation of day length and temperature and the application of growth inhibitors with care.

As a result of the specific hybridization previously mentioned, my new and distinct variety of azalea plant is characterized by its earliness to bloom without artificially induced dormancy, the vigorous plant growth, the strong to deep purplish pink color of its blooms, its readiness to set buds, good formal appearance and good keeping quality.

One of the characteristics of the azalea plant of my invention which is particularly noticeable, is the deep purplish pink of the center of its flower, lightening to a strong pink toward the edges with certain strong purplish red spotting toward the throat.

More specifically, the blooms of my new variety are of a strong to deep purplish pink color (Nickerson Color Fan published by the Munsell Color Company), and as grown in the vicinity of Whitewater, Wisconsin, under uniform culture, plants of this variety grow for commercial purposes about 12 inches in height and with a spread up to 15 inches at the end of two years.

My new variety when grown in the region of Whitewater, Wisconsin, is vigorous with foliage approximating 2 inches in length and over one inch in width with strong stems and between a brilliant yellow green and strong yellow green color.

My new variety has been asexually reproduced by cuttings from tops or segments of mature branches in the vicinity of Whitewater, Wisconsin, and said new variety has been found to retain its distinctive characteristics through successive asexual reproduction.

The accompanying drawing forming a part hereof shows a typical plant and a flower of my new variety of azalea.

The following is a detailed description of my new variety of azalea plant, the color references being to the Nickerson Color Fan published by the Munsell Color Company:

*Description*

Parentage:

*Seed parent.*—Nancy Kay (unpatented, my own hybridization).

*Pollen parent.*—Rosa (unpatented, my own hybridization).

*Flower*

Blooming habit: Once early season and profusely. Can be flowered anytime of year.

Bud:

*Size.*—Medium.

*Form.*—Ovoid. Bud not affected by hot or wet weather.

Color:

*When sepals first divide.*—Between 7.5 R.P. 7/10 and 6/12.

*When petals begin to unfurl.*—Between 7.5. R.P. 7/10 and 6/12.

*When half blown.*—Inside of petals—between 7.5 R.P. 7/10 and 6/12. Reverse of petals—between 7.5 R.P. 7/10 and 6/12 but closer to 7/10.

*Sepals.*—Smooth edge, drop off soon after bud opens.

*Peduncle.*—Length — short. Aspect — smooth. Strength—bending. Bud opens well but tends to dry and wilt in extreme heat as for example above 90 degrees or in cold below 32 degrees.

Bloom:

*Size.*—Large.

*Average size when fully expanded.*—About 2½ inches, maximum of 3 inches.

*Borne.*—Several together.

*Stems.*—Short, normal.

*Form.*—When first open—cupped. Permanence—retains its form to the end.

*Petalage.*—Single hose-in-hose.

*Color.*—Center of flower—between 7.5 R.P. 7/10 and 6/12. Outer petals—more toward 7.5 R.P. 7/10. Base of petals—more toward 7.5 R.P. 6/12. Inside of petals—between 7.5 R.P. 7/10 and 6/12. Reverse of petals—between 7.5 R.P. 7/10 and 6/12. General tonality from a distance—between 7.5 R.P. 7/10 and 6/12. Some of flowers being dotted or blotched 7.5 R.P. 5/12 and 4/10.

*Discoloration.*—Generally retains its color to the end of the third week but some tissue deterioration at the edges at that time.

Petals:

*Texture.*—Soft. Not adversely affected by hot or wet weather unless excessively hot or wet when may develop burnt edges in heat above 90 degrees.

*Appearance.*—Inside—satiny. Outside—satiny.

*Form.*—Round and notched.

*Arrangement.*—Imbricated. No petaloids in center.

*Persistence.*—Hang on and dry.

*Fragrance.*—None.

*Lastingness.*—On the plant—long. As cut flower—fair.

Reproductive organs:

*Stamens, anthers.*—Small, degenerate—10 or less. Color—between 7.5 R.P. 4/11 and 3/4.

*Stamens, filaments.*—Short. Color—7.5 R.P. about 7/10.

*Styles.*—Columnar, of medium length and thin.

*Stigmas.*—Between 7.5 R.P. 7/10 and 6/12.

Fruit: The plant does not bear fruit.

Plant:

*Form.*—Bush.

*Growth.*—Vigorous and compact.

*Height.*—Average plant in commercial production 12 inch height and 15 inch spread.

Foliage:

*Leaflets.*—Single.

*Size.*—Medium, somewhat less than 2" long and 1⅛" wide on the average.

*Quantity.*—Normal.

*New foliage color.*—Upper side—5 G.Y. 6/8. Underside—between 5 G.Y. 6/8 and 7/10.

*Shape.*—Oval pointed.

*Texture.*—Upper side—glossy.

*Ribs and veins.*—Slightly impressed.

*Edge.*—Smooth.

*Leaf stem.*—Color—between 5 G.Y. 6/8 and 7/10.

*Under side.*—Smooth.

Wood (new): Color—between 2.5 G.Y. 7/10 and 6/8.

Wood (old): Color—between 2.5 Y.R. 5/9 and 4/7.

I claim:

A new and distinct variety of azalea plant characterized as to novelty by its earliness to bloom without artificially inducing dormancy, vigorous plant growth, the strong to deep purplish pink color of its blooms, its readiness to set buds, good formal appearance, and good keeping qualities.

No references cited.

ANTONIO F. GUIDA, *Acting Primary Examiner.*

R. E. BAGWILL, *Assistant Examiner.*